(12) United States Patent
Schmidt

(10) Patent No.: US 9,982,027 B2
(45) Date of Patent: May 29, 2018

(54) CONTROL OF RHEOLOGICAL PROPERTIES OF MIXED HYALURONATE/LUBRICIN SOLUTIONS

(71) Applicant: Lubris, LLC, Framingham, MA (US)

(72) Inventor: Tannin Avery Schmidt, Calgary (CA)

(73) Assignee: Lubris LLC, Framingham, MA (US)

( * ) Notice: Subject to any disclaimer, the term of this patent is extended or adjusted under 35 U.S.C. 154(b) by 0 days. days.

(21) Appl. No.: 15/028,752

(22) PCT Filed: Aug. 22, 2014

(86) PCT No.: PCT/US2014/052272
§ 371 (c)(1),
(2) Date: Apr. 12, 2016

(87) PCT Pub. No.: WO2015/060935
PCT Pub. Date: Apr. 30, 2015

(65) Prior Publication Data
US 2016/0250286 A1    Sep. 1, 2016

Related U.S. Application Data

(60) Provisional application No. 61/894,366, filed on Oct. 22, 2013.

(51) Int. Cl.
| | | |
|---|---|---|
| A61K 38/17 | (2006.01) |
| C07K 14/47 | (2006.01) |
| A61K 9/00 | (2006.01) |
| A61K 31/728 | (2006.01) |
| A61K 47/36 | (2006.01) |
| C12P 21/00 | (2006.01) |

(52) U.S. Cl.
CPC .......... *C07K 14/4725* (2013.01); *A61K 9/008* (2013.01); *A61K 9/0014* (2013.01); *A61K 9/0019* (2013.01); *A61K 9/0048* (2013.01); *A61K 31/728* (2013.01); *A61K 38/1709* (2013.01); *A61K 47/36* (2013.01); *C12P 21/005* (2013.01)

(58) Field of Classification Search
None
See application file for complete search history.

(56) References Cited

U.S. PATENT DOCUMENTS

| | | | |
|---|---|---|---|
| 6,530,956 B1 * | 3/2003 | Mansmann | A61F 2/30756 623/18.11 |
| 6,743,774 B1 | 6/2004 | Jay | |
| 6,960,562 B2 | 11/2005 | Jay | |
| 7,001,881 B1 | 2/2006 | Jay | |
| 7,129,062 B2 | 10/2006 | Mermod et al. | |
| 7,415,381 B2 | 8/2008 | Jay | |
| 7,456,275 B2 | 11/2008 | Shimoboji | |
| 7,618,941 B2 * | 11/2009 | Jay | C07K 14/475 514/1.1 |
| 8,026,346 B2 | 9/2011 | Jay | |
| 8,252,917 B2 | 8/2012 | Mermod et al. | |
| 8,506,944 B2 | 8/2013 | Sullivan et al. | |
| 8,551,467 B2 | 10/2013 | Sullivan et al. | |
| 8,563,028 B2 | 10/2013 | Sullivan et al. | |
| 8,680,057 B2 | 3/2014 | Jay | |
| 8,945,604 B2 | 2/2015 | Sullivan et al. | |
| 8,980,840 B2 | 3/2015 | Truitt, III et al. | |
| 9,107,885 B2 | 8/2015 | Sullivan et al. | |
| 9,138,457 B2 | 9/2015 | Sullivan et al. | |
| 9,248,161 B2 | 2/2016 | Sullivan et al. | |
| 9,393,285 B2 | 7/2016 | Sullivan et al. | |
| 9,421,241 B2 | 8/2016 | Sullivan et al. | |
| 9,585,936 B2 | 3/2017 | Sullivan et al. | |
| 2006/0240037 A1 | 10/2006 | Fey et al. | |
| 2007/0111327 A1 | 5/2007 | Jay | |
| 2007/0249557 A1 * | 10/2007 | Jay | A61K 31/728 514/54 |
| 2008/0139458 A1 | 6/2008 | Jay et al. | |
| 2008/0287369 A1 | 11/2008 | Jay | |
| 2009/0068247 A1 | 3/2009 | Jay | |

(Continued)

FOREIGN PATENT DOCUMENTS

| | | |
|---|---|---|
| WO | WO-2005/000331 A2 | 1/2005 |
| WO | WO-2008/143816 A1 | 11/2008 |
| WO | WO-2009/137217 A2 | 11/2009 |
| WO | WO-2011/050287 A1 | 4/2011 |
| WO | WO-2015/081121 A1 | 6/2015 |
| WO | WO-2016/123123 A1 | 8/2016 |
| WO | WO-2016/187414 A1 | 11/2016 |

OTHER PUBLICATIONS

Saurabh Das, Xavier Banquy, Bruno Zappone, George W. Greene, Gregory D. Jay, and Jacob N. Israelachvili, Synergistic Interactions between Grafted Hyaluronic Acid and Lubricin Provide Enhanced Wear Protection and Lubrication, Biomacromolecules, 2013, 14, 1669-1677.*

Nicole Gerwin, Caroline Hops, and Andrea Lucke, Intraarticular drug delivery in osteoarthritis, Advanced Drug Delivery Reviews, 2006, 58, 226-242.*

Flannery, et al., Prevention of cartilage degeneration in a rat model of osteoarthritis by intraarticular treatment with recombinant lubricin, Feb. 26, 2009, Arthritis and Rheumatology, vol. 60, No. 3, Mar. 2009, pp. 840-847.*

Teeple, et al., Effects of Supplemental Intra-articular Lubricin and Hyaluronic Acid on the Progression of Posttraumatic Arthritis in the Anterior Cruciate Ligament-Deficient Rat Knee, The American Journal of Sports Medicine, vol. 39, No. 1.*

(Continued)

*Primary Examiner* — Lianko G Garyu
*Assistant Examiner* — Khalid Kader
(74) *Attorney, Agent, or Firm* — Goodwin Procter LLP

(57) ABSTRACT

Disclosed are mixed solutions of PRG4 and hyaluronic acids having controlled, enhanced rheological properties adapted for various particular medical and cosmetic uses. Such solutions combine the solution-based lubrication ability of HA and the boundary-based lubricating effects of lubricin. Being more viscous, the solutions when used for joint viscosupplementation enhance both the duration of the HA within the joint capsule (in vivo half-life) and enhance the cushioning effects of the HA, as well as improve both solution and boundary mode lubrication mechanisms.

7 Claims, 3 Drawing Sheets

(56) References Cited

U.S. PATENT DOCUMENTS

| | | | |
|---|---|---|---|
| 2009/0104148 A1* | 4/2009 | Jay | A61K 31/728 424/85.2 |
| 2009/0155200 A1 | 6/2009 | Jay | |
| 2010/0092452 A1 | 4/2010 | Sullivan et al. | |
| 2010/0204087 A1 | 8/2010 | Jay | |
| 2011/0059902 A1 | 3/2011 | Sullivan et al. | |
| 2011/0061117 A1 | 3/2011 | Mermod et al. | |
| 2011/0142908 A1 | 6/2011 | Sullivan et al. | |
| 2012/0052077 A1 | 3/2012 | Truitt, III et al. | |
| 2012/0134925 A1 | 5/2012 | Sullivan et al. | |
| 2012/0231449 A1 | 9/2012 | Mermod et al. | |
| 2012/0321693 A1 | 12/2012 | Sullivan et al. | |
| 2013/0039865 A1 | 2/2013 | Truitt, III et al. | |
| 2013/0116186 A1 | 5/2013 | Jay | |
| 2013/0143264 A1 | 6/2013 | Nicolas et al. | |
| 2013/0315973 A1 | 11/2013 | Jay | |
| 2014/0179611 A1 | 6/2014 | Jay | |
| 2016/0235809 A1 | 8/2016 | Sullivan et al. | |
| 2016/0304572 A1 | 10/2016 | Schmidt et al. | |

OTHER PUBLICATIONS

Kwiecinski, The effect of molecular weight on hyaluronan s cartilage boundary lubricating ability alone and in combination with proteglycan 4, Osteoarthritis and Cartilage, Jul. 29, 2011, pp. 1356-1362, vol. 19, No. 11, Bailliere Tindall, London, GB.

Jay et al, Comparison of the boundary-lubricating ability of bovine synovial fluid, lubricin, and healon, The Journal of Biomedical Materials Research, Jun. 5, 1998, pp. 414-418, vol. 40, No. 3, Wiley, New York, US.

Lotz, Osteoarthritis year 2011 in review: biology, Osteoarthritis and Cartilage, Mar. 1, 2021, pp. 192-196, vol. 20, No. 3.

Gregory et al, Prevention of cartilage degeneration and restoration of chondroprotection by lubricin tribosupplementation in the rat following anterior cruciate ligament transection, Arthritis & Rheumatism, Aug. 6, 2010, pp. 2382-2391, vol. 62, No. 8.

International Search Report for International Patent Application No. PCT/US2014/052272 dated Dec. 18, 2014 (4 pages).

Written Opinion of the International Searching Authority for International Patent Application No. PCT/US2014/052272 dated Dec. 18, 2014 (6 pages).

Balazs et al., (1967), "Hyaluronic acid in synovial fluid. I. Molecular parameters of hyaluronic acid in normal and arthritis human fluids," Arthritis Rheum., 10(4):357-76.

Larsen and Balazs, (1991), "Drug delivery systems using hyaluronan and its derivatives," *Adv. Drug Delivery Rev.*, 7(2):279-293.

Simon, (1999), "Viscosupplementation therapy with intra-articular hyaluronic acid. Fact or fantasy?," *Rheum. Dis. Clin. North. Am.*, 25(2):345-57.

Nishimura et al., (1998), "Role of chondroitin sulfate-hyaluronan interactions in the viscoelastic properties of extracellular matrices and fluids," Biochim. Biophys. Acta., 1380(1):1-9.

Jay et al., (2001), "Boundary lubrication by lubricin is mediated by O-linked Beta(1-3)Gal-GalNAc oligosaccharides," Glycoconjugate Journal, 18:807-815.

Jay et al., (2007), "The role of lubricin in the mechanical behavior of synovial fluid," *Proc. Natl. Acad. Sci. USA*, 104(15):6194-6199.

Jay et al., (2007), "Association Between Fiction and Wear in Diarthrodial Joints Lacking Lubricin," *Arthritis and Rheumatism*, 56(11):3662-3669.

Jay et al., (2001), "Homology of lubricin and superficial zone protein (SZP): products of megakaryocyte stimulating factor (MSF) gene expression by human synovial fibroblasts and articular chondrocytes localized to chromosome 1q25," J. Orthopaedic Res., 19:677-687.

Jay et al., (2004), "Lubricin and surfacing of articular joints," Curr. Opin. Orthop., 15:355-359.

Schmidt et al., (2007), "Boundary Lubrication of Articular Cartilage," Arthritis and Rheumatism, 56(3):882-891.

Schmidt et al., (2009), "Disulfide-bonded multimers of proteoglycan 4 (PRG4) are present in normal synovial fluids," Biochimica et Biophysica Acta, 1790:375-384.

* cited by examiner

Fig. 2 Viscosity control of hrPRG4 + 1.5 MDa HA, C* = 1.0 mg/ml

SEQUENCE LISTING

<160> NUMBER OF SEQ ID NOS: 2

<210> SEQ ID NO 1
<211> LENGTH: 1404
<212> TYPE: PRT
<213> ORGANISM: Homo sapiens

<400> SEQUENCE: 1

```
Met Ala Trp Lys Thr Leu Pro Ile Tyr Leu Leu Leu Leu Ser Val
1               5                   10                  15
Phe Val Ile Gln Gln Val Ser Ser Gln Asp Leu Ser Ser Cys Ala Gly
            20                  25                  30
Arg Cys Gly Glu Gly Tyr Ser Arg Asp Ala Thr Cys Asn Cys Asp Tyr
            35                  40                  45
Asn Cys Gln His Tyr Met Glu Cys Cys Pro Asp Phe Lys Arg Val Cys
    50                  55                  60
Thr Ala Glu Leu Ser Cys Lys Gly Arg Cys Phe Glu Ser Phe Glu Arg
65                  70                  75                  80
Gly Arg Glu Cys Asp Cys Asp Ala Gln Cys Lys Lys Tyr Asp Lys Cys
                85                  90                  95
Cys Pro Asp Tyr Glu Ser Phe Cys Ala Glu Val His Asn Pro Thr Ser
                100                 105                 110
Pro Pro Ser Ser Lys Lys Ala Pro Pro Ser Gly Ala Ser Gln Thr
            115                 120                 125
Ile Lys Ser Thr Thr Lys Arg Ser Pro Lys Pro Asn Lys Lys Lys
    130                 135                 140
Thr Lys Lys Val Ile Glu Ser Glu Glu Ile Thr Glu Glu His Ser Val
145                 150                 155                 160
Ser Glu Asn Gln Glu Ser Ser Ser Ser Ser Ser Ser Ser Ser Ser
                165                 170                 175
Ser Thr Ile Arg Lys Ile Lys Ser Ser Lys Asn Ser Ala Ala Asn Arg
                180                 185                 190
Glu Leu Gln Lys Lys Leu Lys Val Lys Asp Asn Lys Lys Asn Arg Thr
                195                 200                 205
Lys Lys Lys Pro Thr Pro Lys Pro Pro Val Val Asp Glu Ala Gly Ser
            210                 215                 220
Gly Leu Asp Asn Gly Asp Phe Lys Val Thr Thr Pro Asp Thr Ser Thr
225                 230                 235                 240
Thr Gln His Asn Lys Val Ser Thr Ser Pro Lys Ile Thr Thr Ala Lys
                245                 250                 255
Pro Ile Asn Pro Arg Pro Ser Leu Pro Pro Asn Ser Asp Thr Ser Lys
                260                 265                 270
Glu Thr Ser Leu Thr Val Asn Lys Glu Thr Thr Val Glu Thr Lys Glu
            275                 280                 285
Thr Thr Thr Thr Asn Lys Gln Thr Ser Thr Asp Gly Lys Glu Lys Thr
            290                 295                 300
Thr Ser Ala Lys Glu Thr Gln Ser Ile Glu Lys Thr Ser Ala Lys Asp
305                 310                 315                 320
Leu Ala Pro Thr Ser Lys Val Leu Ala Lys Pro Thr Pro Lys Ala Glu
                325                 330                 335
Thr Thr Thr Lys Gly Pro Ala Leu Thr Thr Pro Lys Glu Pro Thr Pro
                340                 345                 350
Thr Thr Pro Lys Glu Pro Ala Ser Thr Thr Pro Lys Glu Pro Thr Pro
                355                 360                 365
Thr Thr Ile Lys Ser Ala Pro Thr Thr Pro Lys Glu Pro Ala Pro Thr
                370                 375                 380
Thr Thr Lys Ser Ala Pro Thr Thr Pro Lys Glu Pro Ala Pro Thr Thr
385                 390                 395                 400
Thr Lys Glu Pro Ala Pro Thr Thr Pro Lys Glu Pro Ala Pro Thr Thr
                405                 410                 415
Thr Lys Glu Pro Ala Pro Thr Thr Thr Lys Ser Ala Pro Thr Thr Pro
```

```
            420                 425                 430
Lys Glu Pro Ala Pro Thr Thr Pro Lys Lys Pro Ala Pro Thr Thr Pro
                435                 440                 445
Lys Glu Pro Ala Pro Thr Thr Pro Lys Glu Pro Thr Pro Thr Thr Pro
            450                 455                 460
Lys Glu Pro Ala Pro Thr Thr Lys Glu Pro Ala Pro Thr Thr Pro Lys
465                 470                 475                 480
Glu Pro Ala Pro Thr Ala Pro Lys Lys Pro Ala Pro Thr Thr Pro Lys
                485                 490                 495
Glu Pro Ala Pro Thr Thr Pro Lys Glu Pro Ala Pro Thr Thr Thr Lys
            500                 505                 510
Glu Pro Ser Pro Thr Thr Pro Lys Glu Pro Ala Pro Thr Thr Thr Lys
            515                 520                 525
Ser Ala Pro Thr Thr Thr Lys Glu Pro Ala Pro Thr Thr Lys Ser
        530                 535                 540
Ala Pro Thr Thr Pro Lys Glu Pro Ser Pro Thr Thr Lys Glu Pro
545                 550                 555                 560
Ala Pro Thr Thr Pro Lys Glu Pro Ala Pro Thr Thr Pro Lys Lys Pro
                565                 570                 575
Ala Pro Thr Thr Pro Lys Glu Pro Ala Pro Thr Pro Lys Glu Pro
            580                 585                 590
Ala Pro Thr Thr Lys Lys Pro Ala Pro Thr Thr Pro Lys Glu Pro
        595                 600                 605
Ala Pro Thr Pro Lys Glu Thr Ala Pro Thr Thr Pro Lys Lys Leu
    610                 615                 620
Thr Pro Thr Thr Pro Glu Lys Leu Ala Pro Thr Thr Pro Glu Lys Pro
625                 630                 635                 640
Ala Pro Thr Thr Pro Glu Glu Leu Ala Pro Thr Thr Pro Glu Glu Pro
                645                 650                 655
Thr Pro Thr Thr Pro Glu Glu Pro Ala Pro Thr Thr Pro Lys Ala Ala
            660                 665                 670
Ala Pro Asn Thr Pro Lys Glu Pro Ala Pro Thr Thr Pro Lys Glu Pro
            675                 680                 685
Ala Pro Thr Thr Pro Lys Glu Pro Ala Pro Thr Thr Pro Lys Glu Thr
        690                 695                 700
Ala Pro Thr Thr Pro Lys Gly Thr Ala Pro Thr Thr Leu Lys Glu Pro
    705                 710                 715                 720
Ala Pro Thr Thr Pro Lys Lys Pro Ala Pro Lys Glu Leu Ala Pro Thr
                725                 730                 735
Thr Thr Lys Glu Pro Thr Ser Thr Thr Cys Asp Lys Pro Ala Pro Thr
            740                 745                 750
Thr Pro Lys Gly Thr Ala Pro Thr Pro Lys Glu Pro Ala Pro Thr
        755                 760                 765
Thr Pro Lys Glu Pro Ala Pro Thr Thr Pro Lys Gly Thr Ala Pro Thr
    770                 775                 780
Thr Leu Lys Glu Pro Ala Pro Thr Thr Pro Lys Lys Pro Ala Pro Lys
785                 790                 795                 800
Glu Leu Ala Pro Thr Thr Thr Lys Gly Pro Thr Ser Thr Thr Ser Asp
                805                 810                 815
Lys Pro Ala Pro Thr Thr Pro Lys Glu Thr Ala Pro Thr Thr Pro Lys
            820                 825                 830
Glu Pro Ala Pro Thr Thr Pro Lys Lys Pro Ala Pro Thr Thr Pro Glu
        835                 840                 845
```

```
Thr Pro Pro Pro Thr Thr Ser Glu Val Ser Pro Thr Thr Lys
    850                 855                 860

Glu Pro Thr Thr Ile His Lys Ser Pro Asp Glu Ser Thr Pro Glu Leu
865                 870                 875                 880

Ser Ala Glu Pro Thr Pro Lys Ala Leu Glu Asn Ser Pro Lys Glu Pro
                885                 890                 895

Gly Val Pro Thr Thr Lys Thr Pro Ala Ala Thr Lys Pro Glu Met Thr
                900                 905                 910

Thr Thr Ala Lys Asp Lys Thr Thr Glu Arg Asp Leu Arg Thr Thr Pro
            915                 920                 925

Glu Thr Thr Thr Ala Ala Pro Lys Met Thr Lys Glu Thr Ala Thr Thr
            930                 935                 940

Thr Glu Lys Thr Thr Glu Ser Lys Ile Thr Ala Thr Thr Thr Gln Val
945                 950                 955                 960

Thr Ser Thr Thr Thr Gln Asp Thr Thr Pro Phe Lys Ile Thr Leu
            965                 970                 975

Lys Thr Thr Thr Leu Ala Pro Lys Val Thr Thr Thr Lys Lys Thr Ile
                980                 985                 990

Thr Thr Thr Glu Ile Met Asn Lys Pro Glu Glu Thr Ala Lys Pro Lys
            995                 1000                1005

Asp Arg Ala Thr Asn Ser Lys Ala Thr Thr Pro Lys Pro Gln Lys
    1010                1015                1020

Pro Thr Lys Ala Pro Lys Lys Pro Thr Ser Thr Lys Lys Pro Lys
    1025                1030                1035

Thr Met Pro Arg Val Arg Lys Pro Lys Thr Thr Pro Thr Pro Arg
    1040                1045                1050

Lys Met Thr Ser Thr Met Pro Glu Leu Asn Pro Thr Ser Arg Ile
    1055                1060                1065

Ala Glu Ala Met Leu Gln Thr Thr Thr Arg Pro Asn Gln Thr Pro
    1070                1075                1080

Asn Ser Lys Leu Val Glu Val Asn Pro Lys Ser Glu Asp Ala Gly
    1085                1090                1095

Gly Ala Glu Gly Glu Thr Pro His Met Leu Leu Arg Pro His Val
    1100                1105                1110

Phe Met Pro Glu Val Thr Pro Asp Met Asp Tyr Leu Pro Arg Val
    1115                1120                1125

Pro Asn Gln Gly Ile Ile Ile Asn Pro Met Leu Ser Asp Glu Thr
    1130                1135                1140

Asn Ile Cys Asn Gly Lys Pro Val Asp Gly Leu Thr Thr Leu Arg
    1145                1150                1155

Asn Gly Thr Leu Val Ala Phe Arg Gly His Tyr Phe Trp Met Leu
    1160                1165                1170

Ser Pro Phe Ser Pro Pro Ser Pro Ala Arg Arg Ile Thr Glu Val
    1175                1180                1185

Trp Gly Ile Pro Ser Pro Ile Asp Thr Val Phe Thr Arg Cys Asn
    1190                1195                1200

Cys Glu Gly Lys Thr Phe Phe Phe Lys Asp Ser Gln Tyr Trp Arg
    1205                1210                1215

Phe Thr Asn Asp Ile Lys Asp Ala Gly Tyr Pro Lys Pro Ile Phe
    1220                1225                1230

Lys Gly Phe Gly Gly Leu Thr Gly Gln Ile Val Ala Ala Leu Ser
    1235                1240                1245
```

| | | | | | | | | | | |
|---|---|---|---|---|---|---|---|---|---|---|
|Thr|Ala|Lys|Tyr|Lys|Asn|Trp|Pro|Glu|Ser|Val|Tyr|Phe|Phe|Lys|
| |1250| | | | |1255| | | |1260| | | | |

Arg Gly Gly Ser Ile Gln Gln Tyr Ile Tyr Lys Gln Glu Pro Val
    1265                1270                1275

Gln Lys Cys Pro Gly Arg Arg Pro Ala Leu Asn Tyr Pro Val Tyr
    1280                1285                1290

Gly Glu Thr Thr Gln Val Arg Arg Arg Phe Glu Arg Ala Ile
    1295                1300                1305

Gly Pro Ser Gln Thr His Thr Ile Arg Ile Gln Tyr Ser Pro Ala
    1310                1315                1320

Arg Leu Ala Tyr Gln Asp Lys Gly Val Leu His Asn Glu Val Lys
    1325                1330                1335

Val Ser Ile Leu Trp Arg Gly Leu Pro Asn Val Val Thr Ser Ala
    1340                1345                1350

Ile Ser Leu Pro Asn Ile Arg Lys Pro Asp Gly Tyr Asp Tyr Tyr
    1355                1360                1365

Ala Phe Ser Lys Asp Gln Tyr Tyr Asn Ile Asp Val Pro Ser Arg
    1370                1375                1380

Thr Ala Arg Ala Ile Thr Thr Arg Ser Gly Gln Thr Leu Ser Lys
    1385                1390                1395

Val Trp Tyr Asn Cys Pro
    1400

<210> SEQ ID NO 2
<211> LENGTH: 5040
<212> TYPE: DNA
<213> ORGANISM: Homo sapiens

<400> SEQUENCE: 2

```
gcggccgcga ctattcggta cctgaaaaca acgatggcat ggaaaacact tcccatttac      60
ctgttgttgc tgctgtctgt tttcgtgatt cagcaagttt catctcaaga tttatcaagc     120
tgtgcaggga gatgtgggga agggtattct agagatgcca cctgcaactg tgattataac     180
tgtcaacact acatggagtg ctgccctgat ttcaagagag tctgcactgc ggagcttttcc    240
tgtaaaggcc gctgctttga gtccttcgag agagggaggg agtgtgactg cgacgcccaa     300
tgtaagaagt atgacaagtg ctgtccccgat tatgagagtt tctgtgcaga agtgcataat     360
cccacatcac caccatcttc aaagaaagca cctccaacct tcaggagcatc tcaaaccatc    420
aaatcaacaa ccaaacgttc acccaaacca ccaaacaaga agaagactaa gaaagttata    480
gaatcagagg aaataacaga agaacattct gtttctgaaa atcaagagtc ctcctcctcc    540
tcctcctctt cctcttcttc ttcaacaatt tggaaaatca agtcttccaa aaattcagct    600
gctaatagag aattacagaa gaactcaaa gtaaagata caagaagaa cagaactaaa       660
aagaaaccta ccccccaaacc accagttgta gatgaagctg gaagtggatt ggacaatggt    720
gacttcaagg tcacaactcc tgacacgtct accacccaac acaataaagt cagcacatct    780
cccaagatca aacagcaaaa accaataaat cccagaccca gtcttccacc taattctgat    840
acatctaaag agacgtcttt gacagtgaat aaagagacaa cagttgaaac taaagaaact    900
actacaacaa ataaacagac ttcaactgat ggaaagagaa gactacttcc cgctaaagag    960
acacaaagta tagagaaaac atctgctaaa gatttagcac ccacatctaa agtgctggct   1020
aaacctacac ccaagctga aactacaacc aaaggccctg ctctcaccac tcccaaggag   1080
cccacgccca ccactcccaa ggagcctgca tctaccacac ccaaagagcc cacacctacc   1140
```

```
accatcaagt ctgcacccac cacccccaag gagcctgcac ccaccaccac caagtctgca      1200
cccaccactc ccaaggagcc tgcacccacc accaccaagg agcctgcacc caccactccc      1260
aaggagcctg cacccaccac caccaaggag cctgcaccca ccaccaa gtctgcaccc         1320 accactccca aggagcctgc acccaccacc cccaagaagc ctgccccaac taccccaag       1380 gagcctgcac ccaccactcc caaggagcct acacccacca ctcccaagga gcctgcaccc      1440
accaccaagg agcctgcacc caccactccc aaagagcctg cacccactgc ccccaagaag      1500
cctgccccaa ctaccccaa ggagcctgca cccaccactc ccaaggagcc tgcacccacc       1560
accaccaagg agccttcacc caccactccc aaggagcctg cacccaccac caccaagtct      1620
gcacccacca ctaccaagga gcctgcaccc accactacca agtctgcacc caccactccc      1680
aaggagcctt cacccaccac caccaaggag cctgcaccca ccactcccaa ggagcctgca      1740
cccaccaccc ccaagaagcc tgccccaact accccaagg agcctgcacc caccactccc       1800
aaggaacctg cacccaccac caccaagaag cctgcaccca ccgctcccaa agagcctgcc      1860
ccaactaccc caaggagac tgcacccacc accccaaga agctcacgcc caccaccccc        1920
gagaagctcg cacccaccac ccctgagaag cccgcaccca ccaccctga ggagctcgca       1980 cccaccaccc ctgaggagcc cacacccacc acccctgagg agcctgctcc caccactccc      2040
aaggcagcgg ctcccaacac ccctaaggag cctgctccaa ctaccccctaa ggagcctgct    2100 ccaactaccc ctaaggagcc tgctccaact acccctaagg agactgctcc aactacccct      2160
aaagggactg ctccaactac cctcaaggaa cctgcaccca ctactcccaa gaagcctgcc      2220
cccaaggagc ttgcacccac caccaccaag gagcccacat ccaccacctc tgacaagccc      2280
gctccaacta ccccctaaggg gactgctcca actaccccta aggagcctgc tccaactacc    2340
cctaaggagc ctgctccaac tacccctaag gggactgctc caactaccct caaggaacct     2400
gcacccacta ctcccaagaa gcctgccccc aaggagcttg cacccaccac caccaagggg     2460
cccacatcca ccacctctga caagcctgct ccaactacac ctaaggagac tgctccaact     2520
acccccaagg agcctgcacc cactaccccc aagaagcctg ctccaactac tcctgagaca     2580
cctcctccaa ccacttcaga ggtctctact ccaactacca ccaaggagcc taccactatc     2640
cacaaaagcc ctgatgaatc aactcctgag ctttctgcag aacccacacc aaaagctctt     2700
gaaaacagtc ccaaggaacc tggtgtacct acaactaaga ctcctgcagc gactaaacct     2760
gaaatgacta caacagctaa agacaagaca acagaaagag acttacgtac tacacctgaa     2820
actacaactg ctgcacctaa gatgacaaaa gagacagcaa ctacaacaga aaaaactacc     2880
gaatccaaaa taacagctac aaccacacaa gtaacatcta ccacaactca agataccaca     2940
ccattcaaaa ttactactct taaaacaact actcttgcac ccaaagtaac tacaacaaaa     3000
aagacaatta ctaccactga gattatgaac aaacctgaag aaacagctaa accaaaagac     3060
agagctacta attctaaagc gacaactcct aaacctcaaa agccaaccaa agcacccaaa     3120
aaacccactt ctaccaaaaa gccaaaaaca atgcctagag tgagaaaacc aaagacgaca     3180
ccaactcccc gcaagatgac atcaacaatg ccagaattga accctacctc aagaatagca     3240
gaagccatgc tccaaaccac caccagacct aaccaaactc caaactccaa actagttgaa     3300
gtaaatccaa agagtgaaga tgcaggtggt gctgaaggag aaacacctca tatgcttctc     3360
aggccccatg tgttcatgcc tgaagttact cccgacatgg attacttacc gagagtaccc     3420
aatcaaggca ttatcatcaa tcccatgctt tccgatgaga ccaatatatg caatggtaag     3480
ccagtagatg gactgactac tttgcgcaat gggacattag ttgcattccg aggtcattat     3540
```

```
ttctggatgc taagtccatt cagtccacca tctccagctc gcagaattac tgaagtttgg    3600
ggtattcctt cccccattga tactgttttt actaggtgca actgtgaagg aaaaactttc    3660
ttctttaagg attctcagta ctggcgtttt accaatgata taaaagatgc agggtacccc    3720
aaaccaattt tcaaaggatt tggaggacta actggacaaa tagtggcagc gctttcaaca    3780
gctaaatata agaactggcc tgaatctgtg tattttttca agagaggtgg cagcattcag    3840
cagtatattt ataaacagga acctgtacag aagtgccctg aagaaggcc tgctctaaat    3900 tatccagtgt atggagaaat gacacaggtt aggagacgtc gctttgaacg tgctatagga    3960
ccttctcaaa cacacaccat cagaattcaa tattcacctg ccagactggc ttatcaagac    4020
aaaggtgtcc ttcataatga agttaaagtg agtatactgt ggagaggact tccaaatgtg    4080
gttacctcag ctatatcact gcccaacatc agaaaacctg acggctatga ttactatgcc    4140
ttttctaaag atcaatacta taacattgat gtgcctagta gaacagcaag agcaattact    4200
actcgttctg ggcagacctt atccaaagtc tggtacaact gtccttagac tgatgagcaa    4260
aggaggagtc aactaatgaa gaaatgaata taaattttg acactgaaaa acattttatt    4320
aataaagaat attgacatga gtataccagt ttatatataa aaatgttttt aaacttgaca    4380
atcattacac taaaacagat ttgataatct tattcacagt tgttattgtt tacagaccat    4440
ttaattaata tttcctctgt ttattcctcc tctccctccc attgcatggc tcacacctgt    4500
aaaagaaaaa agaatcaaat tgaatatatc ttttaagaat tcaaaactag tgtattcact    4560
taccctagtt cattataaaa aatatctagg cattgtggat ataaaactgt tgggtattct    4620
acaacttcaa tggaaattat tacaagcaga ttaatccctc ttttgtgac acaagtacaa    4680 tctaaaagtt atattggaaa acatggaaat attaaaattt tacacttta ctagctaaaa    4740 cataatcaca aagctttatc gtgttgtata aaaaaattaa caatataatg gcaataggta    4800
gagatacaac aaatgaatat aacactaaa cacttcatat tttccaaatc ttaatttgga    4860
tttaaggaag aaatcaataa atataaaata taagcacata tttattatat atctaaggta    4920
tacaaatctg tctacatgaa gtttacagat tggtaaatat cacctgctca acatgtaatt    4980
atttaataaa actttggaac attaaaaaaa taaattggag gcttaaaaaa aaaaaaaaaa    5040
```

CONTROL OF RHEOLOGICAL PROPERTIES OF MIXED HYALURONATE/LUBRICIN SOLUTIONS

REFERENCE TO RELATED APPLICATIONS

This application claims the benefit of U.S. provisional application Ser. No. 61/894,366, "Physiological Lubrication" filed Oct. 22, 2013.

FIELD OF THE INVENTION

This invention relates to the preparation of solutions of hyaluronic acid and lubricin, or PRG4, of controlled rheological properties, intended for various uses including protection of tissue surfaces, lubrication of various interfacing tissue surfaces, and remediation or replacement of synovial fluid in diseased joints, e.g., in arthritic joints.

BACKGROUND OF THE INVENTION

Hyaluronic acid, also known as hyaluronan or hyaluronate, is a biological polymer within the class of glycosaminoglycans. It is a linear polysaccharide comprising alternating glucuronic acid and N-acetyl glucosamine units. The acid form and hyaluronate salts (such as the sodium, potassium, magnesium, and calcium salts, among others, (hereinafter collectively "hyaluronic acid" or "HA") are viscoelastic materials which can be found throughout the body as part of the extracellular matrix. HA can be isolated from natural sources, including cock combs. It varies in molecular weight from a few kDa up to several MDa (approximately from 5,000 to 20,000,000 Da in vivo). HA binds water and lubricates movable parts of the body, such as joints and muscles. It is an important component of the proteoglycans which impart resilient characteristics to articular cartilage, acts as a resilient filler in the extracellular matrix, and is a primary component of aqueous and vitreous humor and synovial fluid. It helps maintain strength and flexibility of cartilage and acts to cushion impacts. It is used medically for intra-articular injections for relief of joint pain, as a tissue filler, and as a component of various topical preparations including drops for the treatment of eye irritation.

Lubricin, or PRG4, is an endogenous human glycoprotein found in the body often in admixture or association with HA. Lubricin is a major boundary lubricant also found in various tissues and tissue surfaces, and is the chief moiety responsible for the remarkable lubrication between weight-bearing cartilage in articular joints. It has been proposed for administration by injection into the synovium to slow the worsening of arthritis symptoms. See, e.g., U.S. Pat. No. 8,026,346 and published application number US 20090104148. Pending application publication number 20130116186 discloses injection of PRG4 into asymptomatic joints at risk of developing arthritis so as to preserve and enhance joint lubrication, preserve chondrocytes and promote healthy expression of the endogenous lubricin they produce. Lubricin also has been proposed for use as a topical treatment for dry eye disease, and as a treatment for interstitial cystitis, among other uses.

Mixtures of lubricin and HA occur in the body, are known in the art, and have been proposed for A solution for injection into weight-bearing joints (e.g., U.S. Pat. No. 7,001,881, and published application numbers 20070249557 and 20080287369), for tissue lubrication (e.g., US 20110059902) and in eye drops (e.g., 20110059902), among other utilities.

Arthritis is characterized by degenerative or abnormal changes in cartilage and synovium of the joints, and ultimately bone. The most common form of arthritis is osteoarthritis ("OA"), a progressive wearing down of opposing joint surfaces accompanied by inflammation resulting in pain and swelling. It may be idiopathic, can occur following joint trauma, or may develop simply as a result of aging and joint use. Rheumatoid arthritis and other immune modulated joint disease have different etiologies but result in similar morbidity, typically in a compressed time frame.

Treatment of OA generally involves a combination of exercise or physical therapy, lifestyle modification, weight loss, intra-articular steroid injections, and analgesics. If pain becomes debilitating, joint replacement surgery is indicated to improve mobility and quality of life. There is no proven treatment to slow or reverse OA, although animal data suggests that lubricin injections, optionally in combination with HA, may slow the development of OA and reduce joint pain.

The molecular weight of synovial fluid HA molecules in healthy humans lies in the range of about $2 \times 10^5$ to about $10^7$ Da; while its concentration ranges from 1 mg/mL up to about 4 mg/mL (Balazs et al., Arthritis Rheum. 10:357, 1967). The weight average molecular weight of HA in the synovial fluid of patients with arthritis such as OA and rheumatoid arthritis typically are lower than weight average molecular weight in normal synovial fluid. Also, HA fragments are thought to be able to induce an inflammatory responses. HA degradation also is thought to be associated with degradation of the lubricating and shock-absorbing effects of the synovium, and for some OA patients, intra-articular injection of HA or "viscosupplementation" is offered to restore the elastic and viscous properties of synovial fluid and thus attempt to recreate the intra-articular joint homeostasis that is disrupted in the degenerative joint. This provides an additional treatment option to address pain and can delay the need for joint replacement.

The viscoelastic properties of a hyaluronic acid preparation and its residence time in the joint cavity are influenced by its viscosity and therefore its molecular weight. Generally, the higher the molecular weight the greater the residence time and the longer the half-life in the joint. Supplementation with high molecular weight (about 2,000 kDa) HA and with cross-linked HA appear to prolong residence time, so higher molecular weight preparations are preferred, although harder to administer and more expensive. The durability of the effect is in any case limited, and to extend it the HA may be chemically modified, e.g., cross-linked or derivatized. Examples of chemical modifications which may be made to HA include any reaction of an agent with the four reactive groups of HA, namely the acetamido, carboxyl, hydroxyl, and the reducing end. U.S. Pat. No. 7,456,275 disclosed commercially successful partially cross-linked high molecular weight hyaluronic acid which is said to prolong the residence time in vivo.

SUMMARY OF THE INVENTION

The rheological behavior of solutions of HA is very important if not the essence of its functionality and utility in almost all of its known medical and personal care applications. It is often within the skill of the art to adjust viscosity of a given biopolymer solution to a range desired by selection of the structural features of the polymer being formulated or by addition of viscosity modifiers. However, for HA solutions intended for intimate, prolonged contact with an organ or tissue, the engineering options have been limited: selection of molecular weight, selection of concentration, or cross-linking. Generally, exogenous viscosity modifiers are inappropriate in such HA solutions.

It has now been discovered that the mixed aqueous solutions of HA and lubricin can be engineered to exhibit desired viscoelastic properties by informed selection of the molecular weight (weight average) of the HA, its concentration, and the concentration of lubricin. As disclosed in detail below, HA solutions comprising polymers at a concentration and of a molecular weight which place it at or below the "critical concentration," C*, exhibits Newtonian viscosity behavior, while solutions above this critical concentration exhibit non-Newtonian behavior. Depending on the intended use of the solution, either condition may be preferable. This invention provides novel mixtures for various uses having selected viscosity, lubricity, and elasticity characteristics.

In one aspect, the invention provides an aqueous mixed solution comprising HA and unreduced lubricin, i.e., preparations comprising lubricin multimers or dimers. The lubricin is characterized by having been extracted from culture medium supporting growth of cells which express the human PRG4 gene and competent to post translationally glycosylate the expressed protein. It is present at a concentration greater than 10 μg/mL, preferably 45 μg/mL to 500 μg/mL. Higher concentrations of lubricin may be used but appear to be of no additional benefit. The hyaluronic acid is present at a concentration just at or less than its critical concentration when disposed alone in solution. The mixed solution has a viscosity greater than the viscosity of the hyaluronic acid alone. Such solutions are well suited for joint viscosupplementation, other contexts where lubrication and space-filling bulk is needed, and for topical application to tissues and other contexts where surface coverage of a relatively viscous lubricin/HA mixture is desired.

Preferred compositions comprise, for example, solutions of HA having a weight average molecular weight from 100 kDa to 6,000 kDa (6 MDa) present at a concentration from 0.05 mg/ml to 1-2 mg/ml, but each solution always at or below the critical HA concentration before addition of lubricin. Lubricin may be present at from about 10 to 1500 μg/ml. Smaller amounts in this range are preferred as the viscosity enhancement effects and lubricity appear to plateau. Mathematically the HA concentration ([HA]) may be expressed as:

$$0.05 \text{ mg/mL} \leq [HA] \leq c^* = \{2500/(0.0029 \cdot [MW^{0.80}])\} \text{ mg/ml}.$$

In still another aspect, the invention provides a viscosupplementation process comprising administering by injection into a joint capsule, thereby to mix with endogenous degraded hyaluronic acid, a preparation comprising human recombinant lubricin in an amount and at a concentration sufficient to increase the viscosity of the synovium therein. This may be implemented by sampling endogenous synovial fluid within the joint and adjusting the amount or concentration of lubricin administered to the joint so as to assure an increase in viscosity of the synovial fluid. HA of an appropriate molecular weight and amount also may be included in this approach so as to essentially rebuild the lubricating and cushioning properties of degraded synovium in OA patients or patients with similar joint pathology.

Human synovial fluid volumes in healthy joints range from approximately 1-4 ml, and HA concentrations from as low as 0.5 mg/ml to about 3.33 mg/ml. In OA or injured joints up to 90 ml. HA may be present (in severe cases). The molecular weight distribution of HA in synovial fluid of OA patients is typically reduced, with peak HA MW decreasing from 6-7 MDa in healthy synovial fluid. The concentration and molecular weight of HA in human synovial fluid can be determined by joint aspiration to obtain a sample followed by use of ELISA and agarose gel electrophoresis (Ludwig et al, Arthritis Rheumatism 2012). This permits the physician to determine the volume and concentration of lubricin to be added to the joint to increase fluid viscosity.

The compositions of the invention may be used in the preparation of medicaments for the treatment of an articular joint by viscosupplementation, for topical application to a tissue surface, in eye drops for the treatment of dry eye disease, or for application to a surface of an organ or tissue during surgery to inhibit formation of adhesions.

DESCRIPTION

Critical Concentration

HA binds many times more water than is its own mass and forms pseudo plastic, elasto-viscous solutions that behave as soft gels and exhibit so-called shear-dependent viscosity and frequency-dependent elasticity (Larsen and Balazs, Adv. Drug Delivery Rev. 7:279, 1991). At the low magnitude of the shear tension, solutions of high molecular weight HA reveal high viscosity and low elasticity; while at the increasing values of shear tension the solutions become more elastic (Simon, Osteoarthritis 25:345, 1999). Such non-Newtonian behavior of synovial fluid is essential for the lubrication of joints during fast movement. The cartilage surface is covered by a thin film of synovial fluid that fills in fine unevenness of the articular structure. Deficiency of this layer leads to increased friction coefficient between the moving parts of the joint which results in pain (Nishimura et al., Biochim. Biophys. Acta 1380:1, 1998).

The intrinsic viscosity of a HA solution, η, is related to the viscosity-average HA molecular mass (approximately equal to the weight-average molecular mass) by the following equation: $[\eta]=0.0029 \times MW^{0.80}$ where MW is molecular weight in Daltons (Balazs, Amino sugar-containing macromolecules in the tissues of the eye and the ear, The Amino Sugars: The Chemistry and Biology of Compounds Containing Amino Sugars, Academic Press, New York, 1965, pp. 401-460.) Because the solvated domain of a hyaluronan molecule is very large, adjacent molecular domains begin to touch each other and interact strongly at a certain critical concentration, "C*". Onset of molecular coupling can be related directly to intrinsic viscosity, using the expression: $C^*=2.5/[\eta]$ where C is in g/mL. (Morris et al. 1980). Generally, the higher the concentration of HA, and the higher the molecular weight of the HA, the more likely it exhibits non-Newtonian behavior. For a given solution of HA of a given molecular weight, the critical concentration, C*, at which viscous behavior transitions from Newtonian to non-Newtonian, is defined by the Balazs equation, $$C^*(g/mL) = 2.5/0.0029 \times Mw0.80 (Da).$$

By way of example, the Balazs equation predicts the following critical concentrations for the following weight average molecular weight for HA:

| MW (in Da) | C* (in mg/mL) |
|---|---|
| 132K | 6.90 |
| 500K | 2.38 |
| 1M | 1.27 |
| 1.5M | 0.99 |
| 2.0M | 0.78 |

Figure 1:
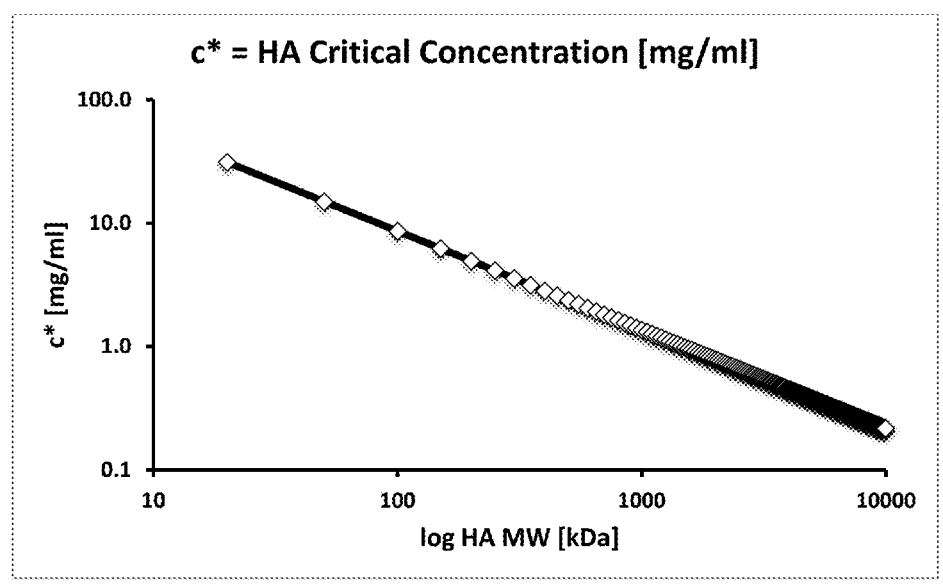
FIG. 1 is a plot relating log C* in mg/mL vs. log MW of hyaluronic acid (HA) in kDa.

More generally, in a solution where the hyaluronic acid (or salt) is at or below the critical concentration, e.g., for a physiologically relevant size approximately 1M Da, equal to or less than about 1.2 mg/ml, or for an HA average MW of 500K, equal to or less than about 2.4 mg/ml, the addition of a lubricin preparation, inclusive of either or all of its dimeric or multimeric forms, will have the effect of increasing viscosity of the solution as compared to the HA solution alone. This viscosity enhancing effect is present and robust at higher lubricin concentrations. Preferably, the lubricin concentration should be, or should be supplemented to be, greater than at least about 10 µg/ml. More preferably, the lubricin preparation is present at a concentration of at least 20 or 30 µg/ml, even more preferably at least a hundred µg/ml, or as much as 400 to 500 µg/ml. Concentrations above this are operable but appear to have no additional effectiveness. Monomeric forms of lubricin appear to lack this viscosity enhancing ability FIG. 1 is a plot relating log C* in mg/mL vs. log MW of HA in kDa. As illustrated, both high concentration of relatively low molecular weight HA and relatively low concentrations of very high molecular weight HA can exceed the critical concentration. Conversely, dilute solutions of high molecular weight HA and more concentrated solutions of lower molecular weight HA can be below the critical concentration and exhibit Newtonian behavior. The states of HA solution above the line are the domain of HA intended for viscosupplementation in arthritic knees—high viscosity, gelatinous, viscoelastic solutions with non-Newtonian flow and elastic shock absorbing properties. The states below the line are the domain of HA intended for cosmetic or topical use, and flow like normal (Newtonian) viscous liquids, and also are candidates for use in preparation of solutions of this invention having increased viscosity.

The synovial fluid of a healthy joint comprises HA of an average molecular weight of about 6 MDa at a concentration of about 0.5-4 mg/mL The critical concentration of the HA, alone in solution, with a molecular weight in this range is less than 1.0 mg/mL, well below the observed HA concentration in healthy human synovial fluid, and accordingly, synovial fluid in a healthy joint consistently exhibits non-Newtonian behavior. Not surprisingly, the current viscosupplementation protocols involve injection of higher molecular weight HA solutions (cross-linked or uncross-linked) at concentrations that seek to assure non-Newtonian behavior and also to promote a longer half-life in vivo.

HA-Lubricin Interaction

The prior art teaches that when lubricin (sometimes referred to as a tribonectin) is formulated with HA, its interaction with the HA reduces the viscosity of the viscosupplement. See, e.g., abandoned US published application number US 20070249557 and US 20080287369. The inventors hereof have discovered that this interaction lies only for HA solutions well into the domain above the critical concentration. For HA solutions having a combination of molecular weight and concentration which place it below the critical concentration, addition of lubricin serves to increase its viscosity, and to bias its behavior toward non-Newtonian viscosity behavior. Such solutions combine the solution-based lubrication ability of HA and the boundary surface-based lubricating effects of lubricin, and being more viscous, enhance both the duration of the HA within the joint capsule (in vivo half-life) and enhance the cushioning effects of the HA.

This synergy was first shown by experiment using bovine lubricin extracted from media conditioned by bovine cartilage explants. Viscosity analyses of solutions containing HA alone, PRG4 alone, and HA+PRG4 were performed with 1.5 MDa HA. Reduction and alkylation to break disulfide bonds in lubricin was performed using dithiothreitol (10 mM) and iodoacetamide (40 mM). Lubricant solutions were prepared by diluting concentrated PRG4 and HA in PBS. Solutions of HA alone and mixtures of HA and PRG4 were prepared contained HA concentrations of 0.3, 1.0, and 3.3 mg/mL, and PRG4 concentrations of 45 and 450 µg/mL. Steady shear viscosity was measured at shear stresses between 0.5-30 Pa with a 5 s measurement interval in a NOVA Rheometer (ATS RheoSystems) at 25° C. and 37° C. with a 40 mm parallel plate geometry and a 0.3 mm gap.

Figure 2:
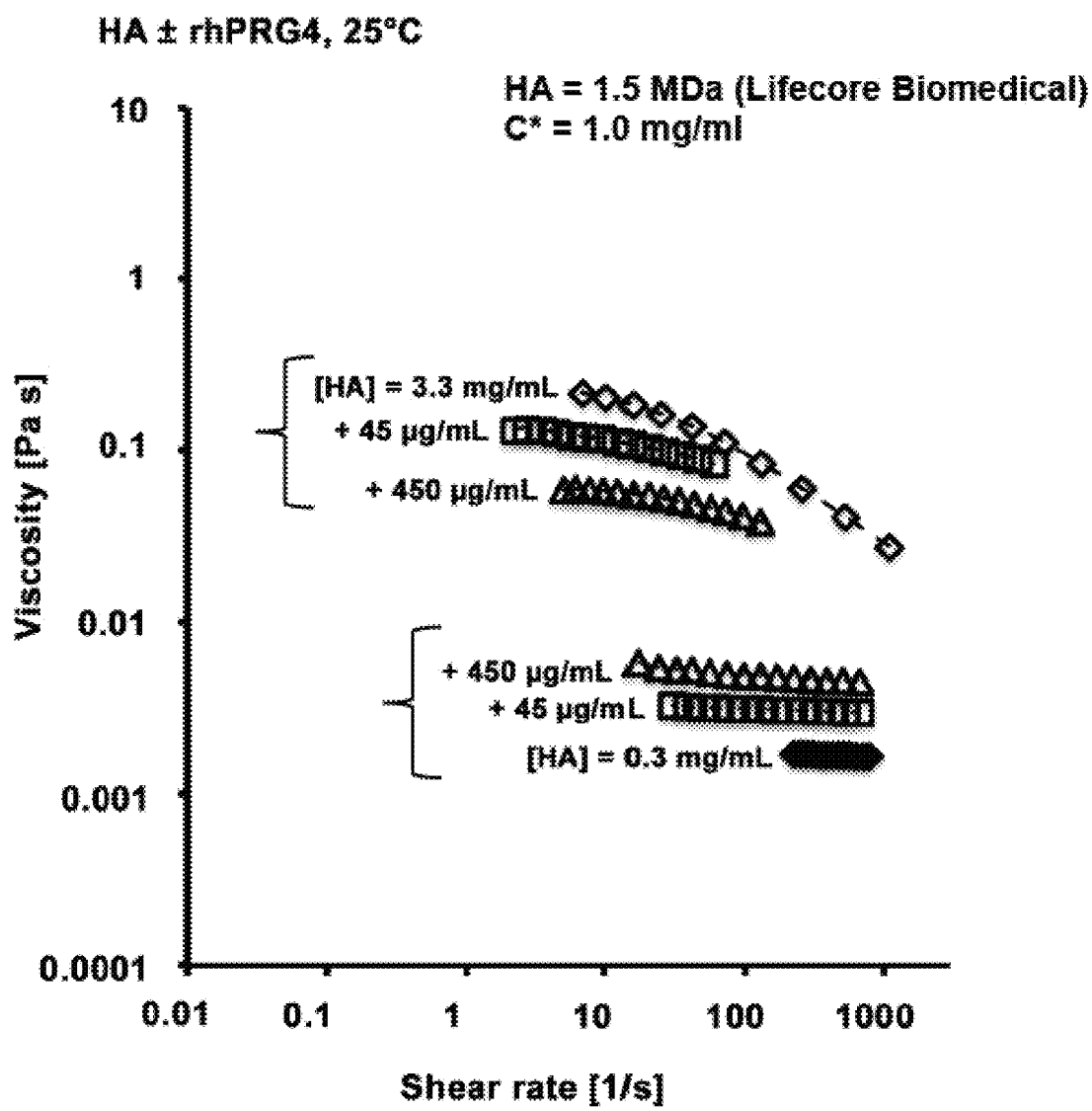
FIG. 2 shows log viscosity in Pascal-seconds vs. log shear rate per second for HA of a molecular weight of 1.5 MDa (C* =1 mg/mL) at two concentrations of HA alone and mixed together with human recombinant lubricin at various concentrations.

The testing was repeated using human, recombinant PRG4. As can be appreciated from the data in FIG. 2 (1 mg/ml HA solution data not shown), the same synergistic effect found with bovine lubricin also applies to human lubricin. FIG. 2 shows log viscosity in Pascal-seconds vs. log shear rate per second for HA of a molecular weight of 1.5 MDa (C*=1 mg/mL) at two concentrations of HA alone and mixed together with human recombinant lubricin at various concentrations. Again, one solution tested was at a concentration well above the critical concentration (3.3 mg/mL), the other well below the critical concentration at 0.3 mg/mL.

As illustrated, the viscosity of 3.3 mg/mL solution of HA alone falls dramatically at an accelerated pace with increasing shear, exhibiting classical non-Newtonian behavior. Addition of 45 µg/mL lubricin reduces the viscosity of the HA solution significantly, although it continues to exhibit non-Newtonian viscous behavior. Addition of 450 µg/mL lubricin reduces the viscosity even further, a bit more than half an order of magnitude lower than the solution of HA alone. Also, its viscosity behavior becomes more Newtonian, with the slope of the curve diminishing.

As expected for an HA solution below the viscosity of the 0.3 mg/mL solution alone is constant with increasing shear, exhibiting classical Newtonian behavior. But unexpectedly, addition of 45 µg/mL lubricin increases the viscosity of the solution significantly, and addition of 450 µg/mL lubricin increases viscosity even further, just less than a half order of magnitude higher than the solution of HA alone. Also, its viscosity appears to start to depart from Newtonian with the slope of the curve diminishing.

At HA MW of 1.5 MDa, concentrations of 0.3 and 1.0 mg/mL, approximately Newtonian behavior is observed; however at 3.3 mg/mL the HA solution exhibits non-Newtonian shear thinning. When PRG4 was added to low concentrations of HA, it increased viscosity in a concentration dependent manner and dependent on the multimeric (at least dimeric) structure of lubricin. For HA concentrations of 0.3 and 1.0 mg/mL, addition of PRG4 at 45 and 450 µg/mL increased viscosity. Viscosities for all solutions of HA plus reduced (monomeric) lubricin were similar to those of HA alone. All samples tested demonstrated a decrease in viscosity at 37° C. relative to 25° C. and increase in viscosity with increasing HA concentration.

This viscosity enhancement is dependent on multimerization but not necessarily the viscosity of PRG4 itself, as enhancement was observed for lubricin at 45 µg/mL, but not reduced lubricin at 450 µs/mL. These results demonstrate that the disulfide bonded structure of PRG4 is essential, and suggest the viscosity enhancing effect is observed in HA solutions at or below their critical concentrations.

Figure 3:
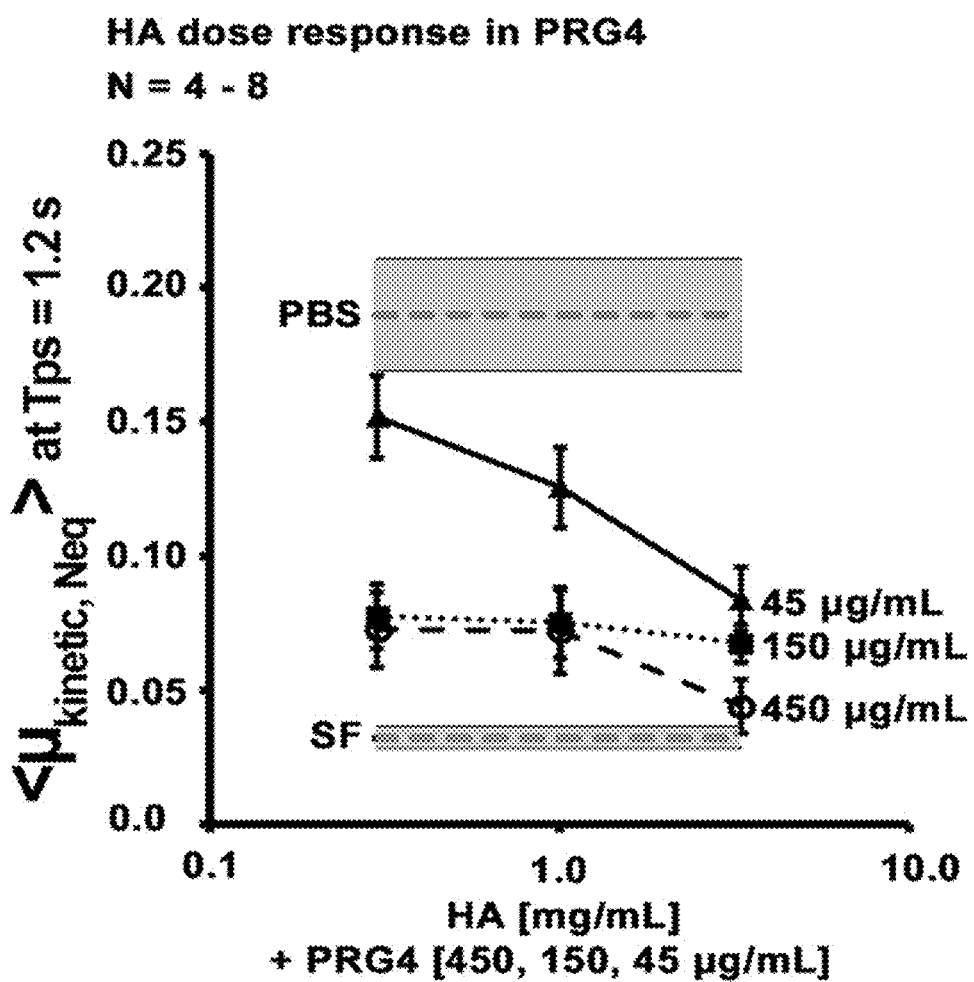
FIG. 3 shows $<\mu_{kinetic, Neq}>$ at Tps =1.2s as a function of HA concentration for HA in the presence of PRG4 at 450, 150, and 45 μg/mL.

FIG. 3 shows $<\mu_{kinetic, Neq}>$ at Tps =1.2s as a function of HA concentration for HA in the presence of PRG4 at 450, 150, and 45 µg/mL.

Lubricin injections alone improve joint function, enhance surface lubrication, and reduce pain. Increasing HA solution viscosity exploiting the synergy with lubricin has two additional important benefits: first, as viscosity increases the fluid-lubrication mode of lubrication increases (or potentially, there is an increase of boundary lubrication through the "viscous boundary layer"); and second, the half-life of intra-capsular HA injections is likely improved. Both effects are advantageous in the context of HA injection into articular joint capsules to temporarily reduce pain and pathologic joint wear.

The control of the rheological properties of mixtures of HA and lubricin exploiting the teaching hereof also permits engineering of solutions having a combination of flow and lubricating properties adapted for various additional uses, such as in eye drops, infusions, injectables, sprays, and gels, e.g., for application to tissue surfaces, for cosmetic injections, or for application to organs or tissues during surgery to inhibit adhesions or to protect tissue surfaces.

The HA Component

Weight average molecular weight values of commercially available HA preparations obtained from various sources vary in the range from hundreds of thousands to approximately 6 million Daltons. Any of these HA products may be used in compositions prepared in accordance with this invention. The HA useful in the present invention is intended to include natural formulations, synthetic formulations, or combinations thereof, and having various molecular weights. Since HA is a polymeric molecule, a given sample can and typically will comprise a range of polymer chains of different lengths and molecular weights. Almost any average of modal molecular weight formulation can be used in the compositions and methods of the invention, including low molecular weight Hyaluronan (from as little as 200 kDa, more likely about 500 kDa to 700 kDa), medium (700 kDa-about 1000 kDa), and high (1.0-4.0 million Daltons (MDa)). In certain exemplary embodiments, the HA has a molecular weight of at least about 500 kDa. It is expected that chemically modified HA's could have very different molecular weights than described above.

The concentration of HA present in the mixture can also vary, but in an exemplary embodiment HA is provided at a pharmaceutically effective amount. In an exemplary embodiment, the HA has a concentration of at least about 1 mg/ml, more preferably at least about 3 to 4 mg/ml, or at least about 10 mg/ml.

The PRG4 Component

The lubricin used in the present invention is multimeric (at least dimeric), preferably full length, heavily glycosylated protein (Sequence ID No. 1) expressed from the human PRG4 gene (Sequence ID No. 2) either in immortalized chondrocytes, in cells modified by gene activation techniques, but preferably in cells transfected using recombinant DNA techniques. Functioning of the protein depends on a multiplicity of O-linked β (1-3) Gal-GalNAc oligosaccharides extending from lubricin's large "mucin like" central domain of 940 amino acids (encoded by exon 6). These were shown to mediate its primary physiological function, boundary lubrication (G. D. Jay, D. A. Harris, C.-J. Cha, Glycoconj J 18, 807 (2001)). It is known that various truncated and mutated isoforms and splice variants of lubricin retain lubricating properties and these also can be used although not preferred. Early attempts at producing recombinant human lubricin essentially were unsuccessful as yields were far too low to be commercially significant. One hypothesis for these failures was that the then current expression technology was incapable of post translationally adding the multiplicity of sugar side chains that must be present to support its lubricating properties. However, more recent technology involving expression in CHO M cells as developed by Selexis SA of Geneva, Switzerland (see: U.S. Pat. Nos. 7,129,062 and 8,252,917, and published application numbers 20110061117, 20120231449 and 20130143264, the disclosures of which are incorporated herein by reference) was discovered unexpectedly to enable production of multiple grams of recombinant human lubricin per liter of culture.

One procedure for the manufacture of human recombinant lubricin useful in the compositions of this invention is set forth below.

a) Vector Construction

The gene encoding the full length 1404 AA human lubricin ("PRG4") was inserted into a plasmid vectors commercially available and proprietary to Selexis SA, Geneva, Switzerland, for enhanced gene expression in mammalian cells. Two expression vectors were constructed. The lubricin gene was cloned into the expression vectors carrying puromycin and the hygromycin resistance. Each vector includes one human X_29 SGE downstream of the expression cassette and an integrated puromycin or hygromycin resistance gene under the control of the SV40 promoter. X_29 SGE refers to Selexis Genetic Elements that are proprietary to Selexis and disclosed in the Selexis patents and applications referenced herein. SGEs shape the chromatin once the expression vector has integrated in the host cell chromosome and thus maintain the transgene in a highly transcriptionally active state. Both expression vectors encode the gene of interest (PRG4) under the control of the hEF-1-alpha promoter coupled to a CMV enhancer. Plasmids were verified by sequencing.

b) Host Cells

The CHO-M cell line is a proprietary Chinese Hamster Ovary cell line derived from CHO-K1 cells (ATCC, Cat. #CCL-61, Lot. 4765275) adapted to serum free cultivation conditions and used for the production of recombinant proteins. See Girod et al, Genome-wide prediction of matrix attachment regions, NATURE METHODS, VOL. 4, NO. 9, September, 2007, p. 747, and Selexis patent and publications identified above relating to matrix attachment regions (MARs), to methods for use of MARs for the development of stable high expressing eukaryotic cell lines such as CHO, and to cells transfected to express proteins involved in translocation of expression products across the ER membrane and/or secretion across the cytoplasmic membrane. CHO-M host cells were cultivated in SFM4CHO medium (HyClone), supplemented with 8 mM L-Glutamine, hypoxanthine and thymidine (1× HT, Invitrogen). Cells were maintained under agitation (120 rpm, 25 mm stroke) in a humidified incubator at 37° C. and 5% CO2.

c) Transfection

The cells were transfected by microporation using a MicroPorator™ (NanoEnTek Inc., Korea) defining the pulse conditions for CHO-M cells (1250V, 20 ms and 3 pulses). Transfection efficiency between 50-70%. The CHO-M cells were first transfected with the puromycin PRG4 expression vector, and stably transfected cells were selected first by culturing on a medium containing puromycin. The expression of recombinant PRG4 was assayed by dot blot analysis. Recombinant PRG4 was detected by means of a polyclonal antibody directed against a lubricin synthetic peptide of PRG4 (Pierce).

Cells from the best performing minipools were next super transfected (additional transfection of already selected minipool population), using the second selection marker, the hygromycin resistance cassette. The same transfection protocol was used as described above. One day after this second transfection, selection was started in SFM4CHO medium, supplemented with 8 mM L-Glutamine and 1× HT, but including 1000 µg/mL of hygromycin. After a media exchange, three pools were transferred to 6-well plates; expanded to spin tubes four days later, and to shake flasks within three days.

d) Clone Generation

The supertransfected pools then were cultivated and analyzed for growth potential in multiple and serial experiments in an attempt to maximize cell properties. The seven best expressing candidates were expanded five days later to suspension cultivation in spin tubes and within five days in shake flasks.

All cell lines were banked. The performance of the three best candidates was compared in shake flasks (seeding 3×105 cells/mL, 20 mL culture volume) within fed-batch cultivation. By day 8, the cultures contained 4.22×106 to 4.95×106 cells/mL and 94% to 96% viability. Cell populations of these pools were diluted for single cell plating. Single colonies were fed by adding 100 µl growth medium per well after 11 days. Eight clones were expanded to suspension cultivation in spin tubes and all eight clones were expanded to shake flasks after one medium exchange (SFM4CHO medium, supplemented with 8 mM L-Glutamine and 1× HT). One subsequent passage was performed before banking of all candidates.

The performance of the five best candidates was compared in shake flasks (seeding 3×105 cells/mL, 20 mL culture volume) with fed-batch cultivation. On day three the cell numbers in the respective cultures ranged from 1.61×106 to 3.46×106 cells/mL with doubling times ranging from 19.8 to 30.7 hours. On day 8, the cell concentrations ranged from 4.02×106 to 9.48×106 cells/mL with cell viability ranging from 88.6% to 97.7%.

In the second experiment, three different super transfected pools were treated to the same procedure as outlined above. This resulted in four clonal cell lines. Again, the performance of these clones was compared in shake flasks, resulting in day 8 cell concentrations ranging from 3.5×106 to 9.48×106 cells/mL and viability between 75.3% and 88.1%.

A clone from the first round selection described above which exhibited on day eight 6.03×106 cells/mL and 95.5% viability was thawed in a shake flask (20 mL working volume). The candidate was transferred to a single plate after one subsequent passage, at the concentration of 200 cell s/mL (1 plate) in the semi-solid medium, including 8 mM L-Glutamine, 1x FIT and Cell Boost 5™, without selection. Plated cells were screened using the ClonePix™ system 12 days later, 84 clones were picked and transferred to 96-well plates. Single colonies were fed by adding 100 µl growth medium per well. Screening of 96-well supernatants took place 18 days after plating. The best 24 growing clones were reset to 24-well plates, and within three days 24-well supernatants were analyzed and 12 clones were transferred to 6-well plates. The six best expressing clones were expanded four days later to suspension cultivation in spin tubes and within four days in shake flasks. Two subsequent passages were performed before banking. Six clonal cell lines were banked.

The performance of six best candidates was compared in shake flasks as described above. On day 8 cell densities ranged between 9.04×106 and 6.40×106 cells/mL and viabilities were between 74.6% and 93.1%. After multiple passages of the clonal pools they were cryopreserved in vials at 6×106 cells/vial and stored in liquid nitrogen.

e) Scaled-Up Cultures

The cell line designated P05ST11-cp05 was selected for scale up. For a 200 liter run, the following conditions are recommended.

| Vessel | XDR-200 Bioreactor |
|---|---|
| pH | 7.1 ± 0.2 |
| Dissolved Oxygen | 50% |
| Temperature | 37° C., see shift notes below |
| Starting Volume | 100 L |
| Inoculum Density | 1e6 VC/mL |
| Base Medium | SFM4CHO Supplemented w/ 1XHT + (8 mM) Glutamax (Gibco ®) |
| Feed | CellBoost 5 (52 g/L) 16% v:v on days 0, 3, 5, 7 *CellBoost5 (52 g/L) 10% v:v days 10 and 12, further if needed. |
| Target culture glucose | Maintain 4-4.5 g/L Feed with 40% stock as required, see notes below |
| WFI Supplementation | As required to maintain Osm ≤410 mOsm/kg, see notes below |
| Harvest Criteria Cell Viability | 60% viability |
| Agitation | 95 RPM |
| Gas Sparge Design | (5) 0.5 mm drilled holes in 2 um porosity disc |

Cell Boost™ Feed
16% of 52 g/L on days 0, 3, 5, 7
10% of 52 g/L on day 10, 12, and further if needed
Glucose/Osmolarity Measurements
measurement protocol: Feed-Measure Glucose-Add Glucose as Necessary-Measure Osmolarity-Add Water as Necessary
Glucose Criteria: 4-4.5 g/L
Osmolarity Criteria: If >410 mOsm, add $H_2O$ to target 390
Glutamax/Glutamine-Monitor Glutamine—if drops to <0.5 mM, supplement to 2 mM
Temperature Shift
Shift to 34 C at 80% or $12×10^6$ cells/ml
Harvest Criteria
Viability<60% f) Purification of Recombinant Human PRG4

Iterative testing resulted in development of a purification procedure set forth below.

Media clarified by sedimentation was diluted with 5 mL 200 mM Tris, 40 mM MgCl2, pH 8.2 and mixed with 400 units of Benzonase (250 units/µl, Novagen) to remove soluble polynucleotides. The solution was mixed for four hours at room temperature, then mixed with 37.8 g urea to adjust urea concentration to 6M, and to result in 120 mL of solution. To this was added 1N NaOH to adjust to pH 11 and 0.01% Tween 20 (sorbitan monolaurate, Sigma).

The post Benzonase material was next treated using GE Q Big Beads™ anion exchange resin with pH of 11 in the presence of 6M Urea and 0.01% Tween 20 run in flow through (FT) mode where the contaminants bind to the resin and the product does not. The column was first sanitized with 0.1N NaOH; then charged with 100 mM NaPO4, 1.5M NaCl, pH 7.2; and re-equilibrated with 200 mM Tris-Borate, 6M Urea, pH 10. The 30 ml volume (XK 26×6 cm) column was then loaded with the 120 ml solution at 4 ml/ml resin at a flow rate of 20 ml/min (240 cm/hr), followed by a wash with equilibration buffer—100 mM Tris-Borate, 100 mM NaCl, 6M Urea, 0.01% Tween 20, pH 11. Shortly after loading, product was collected through the wash (290 mL total volume) until addition of a strip solution 0.1N NaOH+ 1M NaCl.

This partly purified flow-through lubricin pool was pH adjusted with 1M Citrate pH=7.5, and passed through a hydroxyapatite column (BioRad CHT), Column Volume—14 ml (XK 16×7 cm), Column Load—21 ml Load/ml resin, Flow rate=10 ml/min (300 cm/hr). The column was first sanitized with 0.1N NaOH and 1 M NaCl, Charge with 500 mM NaPO4, pH 6.5; re-equilibration with 500 mM NaPO4/ 6M Urea, pH 7.4; and loaded with the 290 mL flow through from the step above. This was followed by wash with equilibration buffer, 15 mM NaPO4, 6M Urea, 0.01% Tween 20, pH 7.4, to produce 305 ml of flow-through containing the product.

The flow through from the hydroxyapatite column was adjusted to pH 4.8 with 1M citrate and diluted with water, then passed through a GE SP Big Bead resin, Column Volume—6 ml (XK 1.6×3 cm), Column Load—58 ml Load/ml resin, Flow rate=6.7 ml/min (200 cm/hr). The column was first sanitized with 0.5N NaOH, charge with 100 mM NaPO4, 1.5M NaCl, pH 7.4; re-equilibration with 50 mM Na citrate/6M urea, 0.01% Tween 20, pH 4.8; and loaded with the 350 mL flow through from the step above. This was followed by wash with equilibration buffer, 50 mM Na citrate/6 M Urea, 0.01% Tween20, pH 4.8, to produce 378 ml of flow-through containing the product. The flow-through was then neutralized with 10N NaOH (pH 7.2).

To concentrate and buffer exchange, the post cationic exchange flow-through product pool was filtered using a 50 kDa molecular weight cut-off TangenX 0.01 m2 flat sheet membrane (TangenX Technology Corporation), LP screen channel. The diafiltration buffer was 10 mM NaPO4, 150 mM NaCl, pH 7.2 (PBS). After sanitization with 0.1N NaOH; a rinsed with MilliQ water; and equilibration with 10 mM NaPO4, 150 mM NaCl, pH 7.2, the membrane was loaded at 15,000 ml/m2; Cross-flow 70 ml/min; transmembrane pressure=6-7 psi; permeate flow=5-6 ml/min to concentrate the solution to approximately 50 ml.

Lastly, the post UFDF product pool was subject to 0.2 µm filtration through a Sartorius Sartopore 2, 150-0.015 m2 membrane at a membrane load of ~17,000 ml/m2, and a flow rate of 45-50 ml/min. The membrane was first primed with 10 mM NaPO4, 150 mM NaCl, pH 7.4, then the product was filtered, followed by a chase filter with ~0.40 ml of buffer and finally the filter was drained.

Absence of contaminating DNAs, rodent viruses, lipopolysaccharide and other pyrogens was confirmed. This procedure can yield at least 0.7-0.9 gram of product per liter of harvested media of approximately 96% purity.

Formulation of Mixtures

Solutions of rhPRG4 and HA may be combined and adjusted to achieve the required concentration and final volume with PBS, pH 7.4, optionally with a small amount of nonionic surfactant such as polyoxyethylene surfactant. Solutions preferably are allowed to equilibrate for several hours at room temperature with nutation. It is also possible to add lyophilized lubricin directly to an HA to formulate a solution of the invention.

In a preferred embodiment, the invention provides a pre-filled syringe, an applicator such as a metered dose spray or drop dispenser, or other container which dispenses a single unit dosage of a sterile composition comprising a solution of the invention. In some embodiments lyophilized HA and lubricin in the appropriate mass ratio is provided that can be readily reconstituted at the point of care. Solutions of course will be adjusted to pH and salt or buffer concentration compatible with the locus of the body at which it is to be used, e.g., normal synovial fluid or the homeostatic osmolarity concentration of healthy eye film.

In accordance with one aspect of the invention it is contemplated that a certain preparations of lubricin and a hyaluronic acid, at the proper ratio and with HA at or below the critical concentration, may be used as a substitute and improvement over HA solutions used alone to treat joint pain. This can result in a longer lasting effect as compared to addition of HA alone, and improved joint lubrication.

Osteoarthritis is known to involve a shift to lower molecular weight species of HA in articular joints such as the knee and the hip. This degraded HA can be removed in whole or in part and replaced with a solution of the invention. Furthermore, it is possible to increase the viscosity of endogenous synovial fluid that has degraded such that it is at or below the critical concentration by intra-articular injection of an amount of lubricin calculated to result in an increase in viscosity. This may be accomplished by a physician who samples synovial fluid from a joint of a patient, and has it analyzed for HA concentration, and weight-average molecular mass (or other parameters indicative of whether the HA is above, below or at the critical concentration), e.g., using electrophoresis or size exclusion chromatography. If the HA concentration is below C*, then the physician supplements the synovial fluid by injection of an amount of lubricin calculated to optimize intrinsic viscosity η, while at the same time increasing both surface mediated and fluid mediated lubrication.

The compositions of the invention also can be administered to a mammal (e.g., a human) to treat soft tissue injuries, structural injuries, and degenerative or congenital conditions such as CACP syndrome. In particular, the compositions of the invention can be administered to a mammal to treat or to alleviate, inhibit, or relieve the symptoms of osteoarthritis (which includes erosive osteoarthritis and is also known as osteoarthrosis or degenerative joint disease or DJD, or early osteoarthritis), rheumatoid arthritis, juvenile rheumatoid arthritis, spondyloarthropathies, gouty arthritis, infectious arthritis, structural joint defects (e.g., torn menisci and cruciate ligaments), synovitis (e.g., traumatic synovitis), and repetitive stress syndromes, as well as inflammation and symptoms associated with Sjogren's syndrome, Crohn's disease, and psoriatic arthritis, and systemic lupus erythematosus.

The compositions of the invention can also be administered to a mammal to alleviate, inhibit, relieve, or treat arthritic conditions associated with spondylitis, including ankylosing spondylitis, reactive arthritis (Reiter's syndrome), arthritis associated with chronic inflammatory bowel disease and AIDS-related seronegative spondyloarthropathy.

The compositions of the invention also can be administered to a mammal to alleviate or inhibit symptoms of rheumatic disease and disorders, e.g., systemic sclerosis and forms of scleroderma, polymyositis, dermatomyositis, necrotizing vasculitis and other vasculopathies, hypersensitivity vasculitis (including Henoch-Schonlein purpura), Wegener's granulomatosis, Giant cell arteritis, mucocutaneous lymph node syndrome (Kawasaki disease), Behcet's syndrome, Cryoglobulinemia, juvenile dermatomyositis, Sjogren's syndrome, overlap syndromes (includes mixed connective tissue disease), polymyalgia rheumatica, erythema nodosum, relapsing polychondritis, tendonitis (tenosynovitis), Bicipital tendonitis, bursitis, Olecranon bursitis, adhesive capsulitis of the shoulder (frozen shoulder) trigger finger, and Whipple's disease.

The compositions of the invention are also useful for alleviating or inhibiting the symptoms of diseases with rheumatic states, including, e.g., gout, pseudogout, chondrocalcinosis, amyloidosis, scurvy, specific enzyme deficiency states (including Fabry's disease, alkaptonuria, ochonosisi, Lesch-Nyhan syndrome, and Gaucher's disease), hyperlipoproteinemias (types II, Ia, IV), Ehlers-Danlos syndrome, Marfan's syndrome, pseudoxanthoma elasticum, and Wilson's disease.

A compositions of the invention can be administered to the joint (e.g., the knee, shoulder, wrist, ankle, or elbow) or connective tissue of a mammal. It is envisioned that the compositions can be administered to treat connective tissue adhesions, e.g., adhesions in the hand or shoulder, and visceral adhesions, which occur after abdominal or thoracic surgery, connective tissue defects, e.g., trigger finger and carpal tunnel syndrome, as well as defects that occur following connective tissue grafts and transfers. The compositions of the invention can be administered to treat other common problems in which adhesion formation or restoration of tissue gliding is a problem.

The compositions of the invention are also useful for alleviating or inhibiting the symptoms of cystitis (see 20120321693), dry mouth (see 20130039865), dry eye disease (see 20110059902). It can also be used in contact lens storage and cleaning solutions (see 20100092452), contact lens coatings (see 20110142908), as a vaginal lubricant (see 20120052077), and as a component of various cosmetics for application to the skin.

Administration of Compositions of the Invention

Standard methods for delivery of the compositions of the invention can be used. Such methods are well known to those of ordinary skill in the art. For intra-articular administration, the endogenous synovial fluid may first be removed and then replaced with 2-6 mL of a composition of the invention, for example comprising 0.9 mg/mL HA of average molecular weight 1.5 MDa, and 450 µg/ml lubricin, preferably administered by injection into a knee joint using a fine (e.g., 14-22 gauge, preferably 18-22 gauge) needle.

The known HA products designed for intra articular injection typically comprise 2-4 mL of HA solution having a concentration of 8-22 mg/ml with HA MW ranging from a low of approximately 500 kDa to a high of about 6 MDa. Most products contemplate a single injection of an HA solution well above the critical concentration. Higher molecular weight HA is more expensive than lower molecular weight materials, so the invention provides an additional option involving HA of a lower MW with enhanced viscosity and added lubricity through the addition of PRG4. For example, one may use from 1-4 mL of HA solutions with MW of HA in the range of 500-1200 kDa and at concentrations of about 1.15 (for the higher weight HA) to 2.35 mg/mL (for the lower), with rhPRG4 added at 45-450 µg/mL. More specifically, for example, 4 ml of 500 kDa HA at 2.35 mg/ml (9.4 mg HA) with 45-450 µg/mL of rhPRG4 (0.18-1.8 mg rhPRG4); or, 4 ml of 1200 kDa HA at 1.15 mg/ml (4.6 mg HA) with 45-450 µg/mL of rhPRG4 (0.18-1.8 mg rhPRG4).

For HA-containing eye drops, typical products range from about 1 mg/mL for 'lite' to up 4 mg/mL for 'gel'. While the molecular weight of the HA in most existing eye drop products is unpublished, it is likely in the range of 500-700 kDa, well below the critical concentration. In any event, the addition of PRG4 to otherwise conventional eye drop formulations both enables control of the viscosity of the eye drop and has a therapeutic/prophylactic effect on eye irritation and various forms and symptoms of dry eye disease. See US 20110059902. For example, the viscosity of solutions of HA with a MW in the range of 100-1000 kDa at concentrations of from 1 mg/mL up to about 8.6 mg/mL may be increased as desired by addition of rhPRG4 added at 45-450 µg/mL. Specifically, for example, a 10 ml bottle of 100 kDa HA at 4 mg/mL (90 mg HA) may include 150 µg/mL of rhPRG4 (0.6 mg rhPRG4); or alternatively, the viscosity of 10 ml of 600 kDa HA at 2 mg/ml (20 mg HA) may be modified with 150 µg/mL of rhPRG4 (0.6 mg rhPRG4).

For skin/vaginal lubricants, for example, HA solutions with MW in the range of 50-500 kDa at concentrations of 5 to 0.05 mg/mL, may be supplemented with rhPRG4 45-450 µg/mL.

For prevention of surgical adhesions, the compositions of the invention may be administered as a coating on a gel, foam, fiber or fabric placed late in surgery to block adhesion formation, but preferably as a spray of suitable viscosity which results in a coating of lubricin/HA over the tissue at risk of adhesion formation.

Other embodiments are within the following claims.

What is claimed is:

1. An aqueous mixed solution comprising:
   unreduced lubricin present at a concentration greater than 10 μg/mL, characterized by having been extracted from culture medium supporting growth of cells which express the human PRG4 gene and competent to post-translationally glycosylate the expressed protein, in admixture with
   hyaluronic acid or a salt thereof having a combination of a weight average molecular weight and concentration placing it at or less than its critical concentration when disposed alone in solution,
   said mixed solution having a viscosity greater than the viscosity of the hyaluronic acid solution in the absence of lubricin.

2. The solution of claim 1, wherein the hyaluronic acid or salt thereof concentration is less than 2.5 mg/mL and the concentration of lubricin is greater than 45 μg/mL.

3. The solution of claim 1, wherein the weight average molecular weight of the hyaluronic acid or salt thereof is less than 1.0 MDa and the concentration of lubricin is greater than 45 μg/mL.

4. The solution of claim 1, wherein the weight average molecular weight of the hyaluronic acid or salt thereof is less than 1.0 MDa and the concentration of lubricin is between 100 and 300 μg/mL.

5. A method of viscosupplementation comprising:
   administering by injection into a joint capsule of a mammal suffering from osteoarthritis thereby to mix with endogenous degraded hyaluronic acid therein a preparation comprising unreduced human recombinant lubricin in an amount and at a concentration sufficient to increase the viscosity of the synovium therein; and
   comprising sampling the endogenous synovial fluid within the joint and adjusting the amount or concentration of the human recombinant lubricin administered to the joint to assure an increase in viscosity of said synovial fluid.

6. The process of claim 5, wherein said preparation also comprises hyaluronic acid or a salt thereof.

7. The method of claim 5, wherein the mammal is a human.

* * * * *